(12) United States Patent
Chen

(10) Patent No.: US 6,656,165 B2
(45) Date of Patent: Dec. 2, 2003

(54) DISPOSABLE SAFETY SYRINGE

(75) Inventor: Cho-Yin Chen, Taichung Hsien (TW)

(73) Assignee: Hsin Cheng Chen, Taichung Hsien (TW)

( * ) Notice: Subject to any disclaimer, the term of this patent is extended or adjusted under 35 U.S.C. 154(b) by 94 days.

(21) Appl. No.: 09/983,839

(22) Filed: Oct. 26, 2001

(65) Prior Publication Data

US 2003/0083627 A1 May 1, 2003

(51) Int. Cl.⁷ .................................................. A61M 5/00
(52) U.S. Cl. ...................................... 604/240; 604/110
(58) Field of Search ............................... 604/48, 93.01, 604/110, 181, 182, 186, 187, 188, 192, 195, 197, 198, 208, 210, 214, 218, 226, 222, 236, 239, 240–243; 128/919

(56) References Cited

U.S. PATENT DOCUMENTS 3,989,044 A * 11/1976 Meierhoefer ................ 604/192
4,950,241 A * 8/1990 Ranford ...................... 604/110
5,256,151 A * 10/1993 Chul ........................... 604/195
5,531,705 A * 7/1996 Alter et al. .................. 604/195
5,997,511 A * 12/1999 Curie et al. .................. 604/195

* cited by examiner

Primary Examiner—LoAn H. Thanh
(74) Attorney, Agent, or Firm—Rosenberg, Klein & Lee

(57) ABSTRACT

A disposable safety syringe includes a barrel, a needle holder and a piston stem. Front end of the barrel is formed with an annular flange for a click hook of a needle holder to hook the flange and locate the needle holder. The needle holder has an inward extending coupling tube formed with multiple axially extending splits. A column section projects from front end of the piston stem will slightly expand the coupling tube. An annular binding groove is formed around the column section. The coupling tube is restricted by the wall of the binding groove to bind and tightly clamp the column section. The click hook thereof is pressed against a conic section of front end of the barrel. At this time, the click hook is converged and the engaging blocks are inlaid into the engaging channels to locate the click hook.

4 Claims, 7 Drawing Sheets

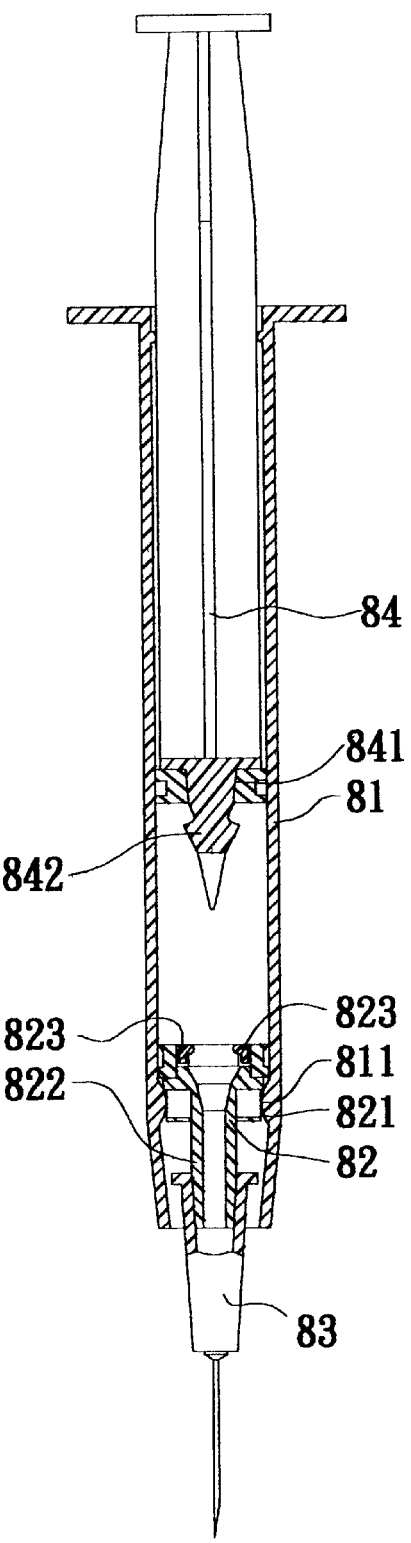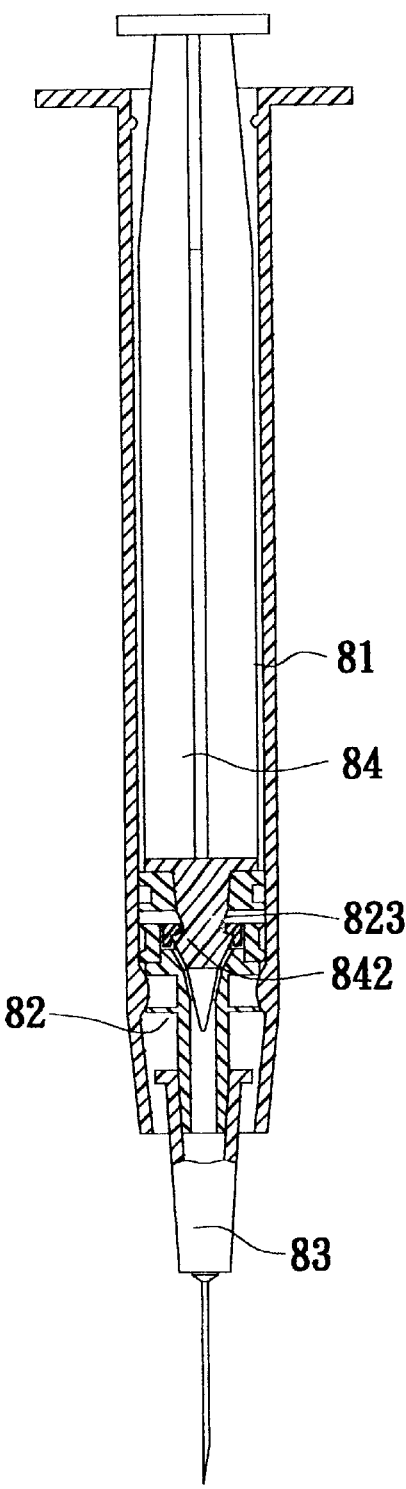
PRIOR ART
FIG. 9
PRIOR ART
FIG. 10

DISPOSABLE SAFETY SYRINGE

BACKGROUND OF THE INVENTION

The present invention is related to a disposable safety syringe. The inner circumference of front end of the barrel of the syringe is formed with a conic section. When the piston stem is forcedly pushed inward to drive the needle holder, the click hooks thereof is pressed against the conic section and converged and located. Accordingly, the piston stem can drive the needle holder to move rearward and make the click hooks pass through the flange of inner circumference of the barrel so as to retract the needle holder into the barrel.

FIG. 9 shows a conventional safety syringe. The inner circumference of front section of the barrel 81 is formed with a flange 811. The needle holder 82 fitted in the barrel 81 is formed with a recessed section 821 corresponding to the flange 811. By means of engagement between the flange 811 and the recessed section 821, the needle holder 82 can be located in the barrel 81. The needle holder 82 has an insertion tube 822 for fitting with an injection needle 83. The inner circumference of the needle holder 82 is formed with two click hooks 823. The front end of the piston 841 of the piston stem 84 is formed with an engaging section 842 corresponding to the click hooks 823.

In use, the injection needle 83 is first fitted with the insertion tube 822 of the needle holder 82. Then, the piston stem 84 is pushed forward to a predetermined position and then pulled rearward so as to suck the medicine into the barrel 81. After injection, the piston stem 84 is pushed forward to make the engaging section 842 fit into the needle holder 82. At this time, the click hooks 823 are engaged with the engaging section 842 to prevent the piston stem 84 from departing from the needle holder 82 as shown in FIG. 10. Accordingly, when pulled rearward, the piston stem 84 can drive the needle holder 82 to move and make the recessed section 821 disengage from the flange 811. Under such circumstance, the needle holder 82 can be retracted into the barrel 81 along with the piston stem 84. Accordingly, the injection needle 83 is prevented from protruding outward so as to avoid impalement of medical personnel.

The needle holder 82 is fixed only by means of the engagement between the flange 811 and the recessed section 821. In the case that the flange 811 more protrudes from the inner circumference of the barrel 81, the flange 811 will be able to more tightly engage with the recessed section 821 to achieve greater fixing force and prevent the needle holder 82 from moving rearward when inserting the injection needle 83. However, after the engaging section 842 of the piston stem 84 is engaged into the needle holder 82, the needle holder 82 will be hard to be driven and retracted into the barrel 81. In the case that the flange 811 less protrudes from the inner circumference of the barrel 81, the flange 811 is not so tightly engage with the recessed section 821 and the fixing force is less. Accordingly, after the engaging section 842 of the piston stem 84 is engaged into the needle holder 82, the needle holder 82 can be easily driven and retracted into the barrel 81. However, when inserting the injection needle 83, the needle holder 82 can be hardly truly fixed in the barrel 81 and is likely to be pushed rearward.

Furthermore, when the piston stem 84 is first pushed forward prior to filling of the medicine or bleeding and then pulled rearward to suck the medicine or blood, it often takes place that the engaging section 842 of the piston stem 84 are engaged with the click hooks 823 of the needle holder 82 without departure. Under such circumstance, the syringe must be discarded to use a new syringe. This leads to waste of resource.

SUMMARY OF THE INVENTION

It is therefore a primary object of the present invention to provide a disposable safety syringe. The inner circumference of front end of the barrel of the syringe is formed with a conic section. When the piston stem is forcedly pushed inward to drive the needle holder, the click hooks thereof is pressed against the conic section and converged and located. Accordingly, the piston stem can drive the needle holder to move rearward and make the click hooks pass through the flange of inner circumference of the barrel so as to retract the needle holder into the barrel and ensure safety.

The present invention can be best understood through the following description and accompanying drawings wherein:

BRIEF DESCRIPTION OF THE DRAWINGS

FIG. 9 is a sectional view of a conventional safety syringe; and

FIG. 10 is a sectional view of the conventional safety syringe, in which the piston stem is engaged with the needle holder.

DETAILED DESCRIPTION OF THE PREFERRED EMBODIMENTS

Figure 1:
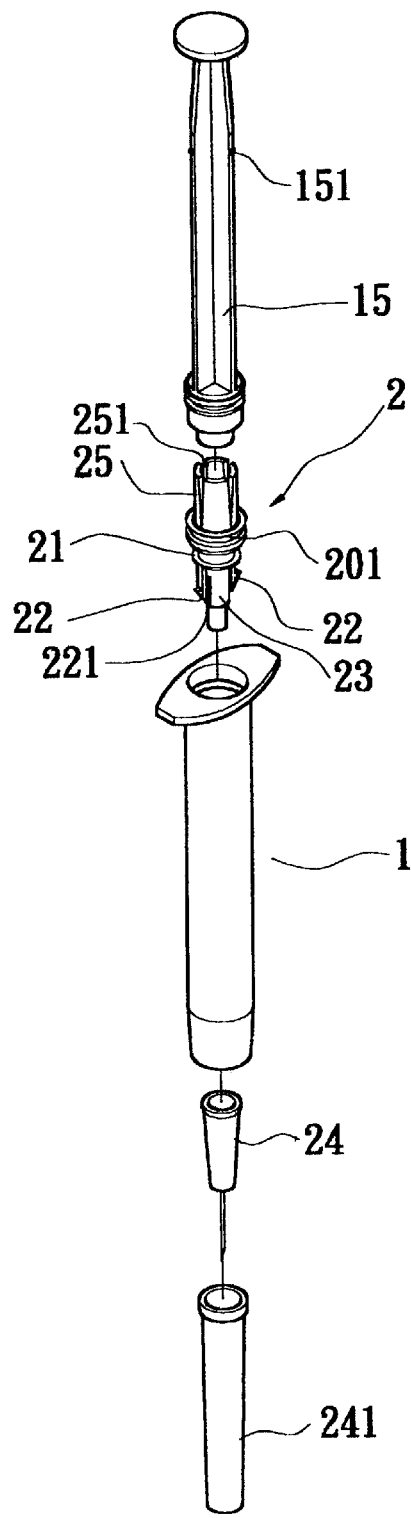
FIG. 1 is a perspective exploded view of the present invention.
Figure 2:
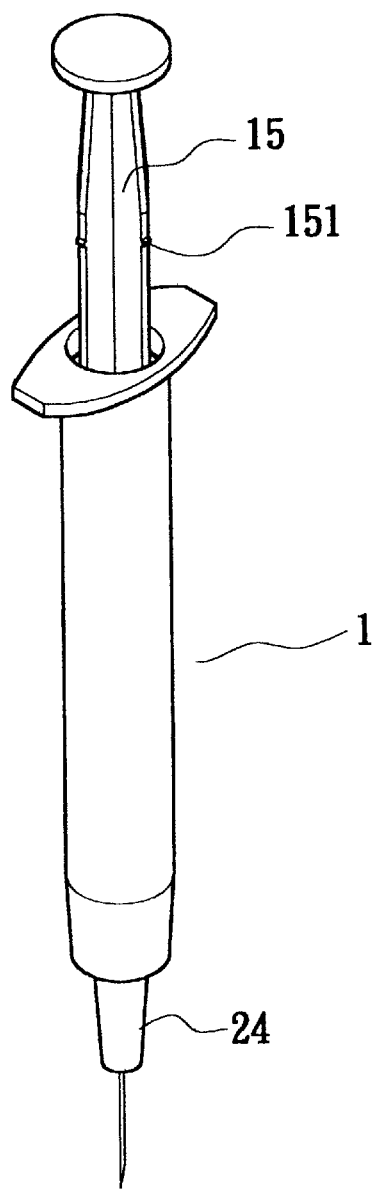
FIG. 2 is a perspective assembled view of the present invention.
Figure 3:
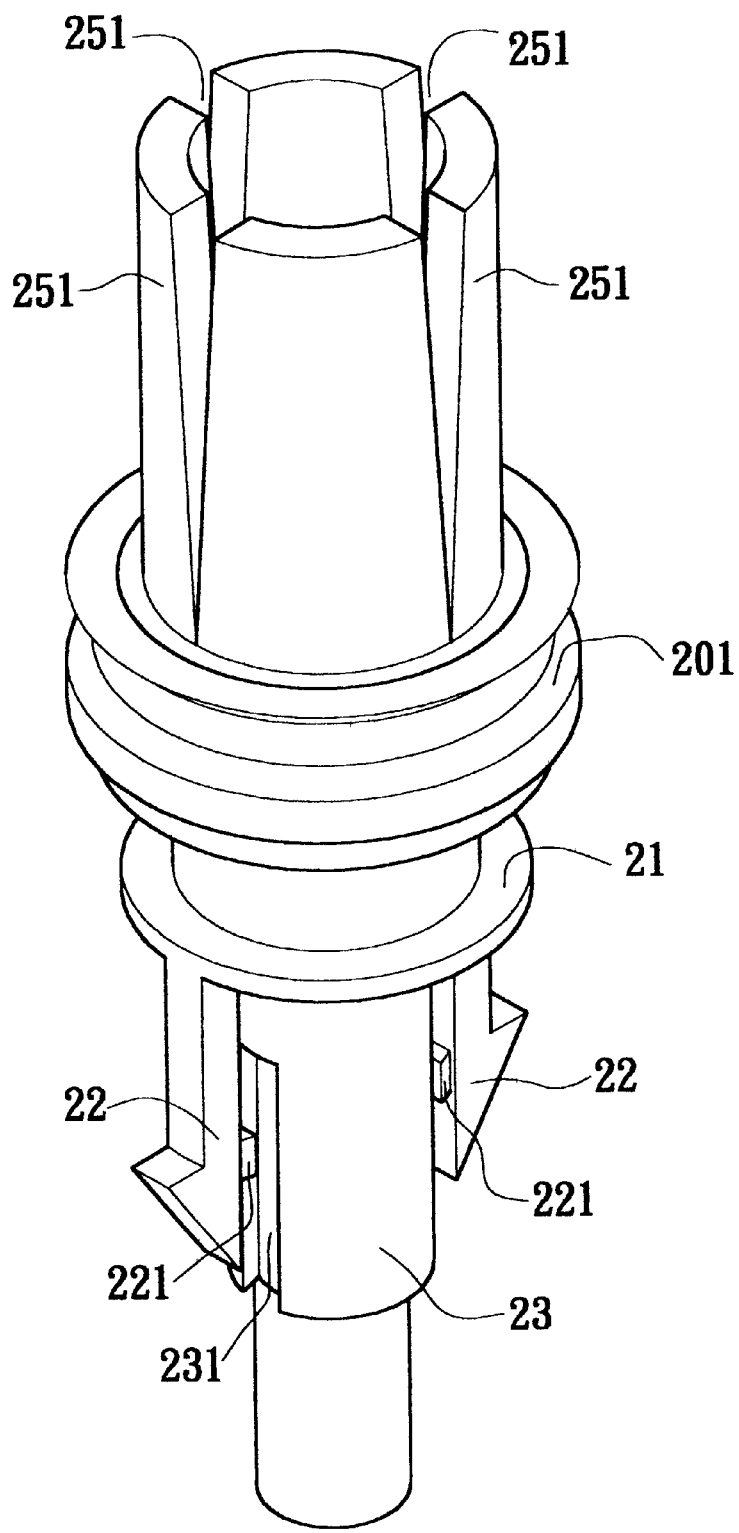
FIG. 3 is a perspective view of the needle holder of the present invention.

Please refer to FIGS. 1 to 4. The disposable safety syringe of the present invention includes a barrel 1, a needle holder 2 and a piston stem 15.

The barrel 1 has a tubular shape. The inner circumference of front section of the barrel 1 is formed with an annular flange 11. The inner circumference of the barrel 1 in front of the flange 11 is tapered to form a conic section 12.

The outer circumference of the needle holder 2 is equipped with a sealing washer 201 plugged in the front section of the barrel 1. The needle holder 2 has a fixing ring 21 having two click hooks 22 for hooking the flange 11 of the barrel 1 to locate the needle holder 2. The needle holder 2 further has an insertion tube 23 protruding from the needle holder 2 for fitting with an injection needle 24 and a needle sheath 241. The insertion tube 23 is formed with two dovetailed engaging channels 231 respectively corresponding to the click hooks 22. Each click hook 22 has a dovetailed engaging block 221 corresponding to the engaging channel 231. When the engaging block 221 is inlaid in the engaging channel 231, the click hook 22 is located. The insertion tube 23 inward extends to form a coupling tube 25 having multiple axially extending splits 251.

The piston stem 15 has a piston 16 plugged in the barrel 1. The piston 16 is equipped with a sealing washer 161. A column section 17 projects from front end of the piston 16. The column section 17 has a diameter corresponding to the inner diameter of the coupling tube 25, whereby when inserted into the coupling tube 25, the column section 17 can slightly expand the coupling tube 25. In addition, the front end of the piston 16 is formed with an annular binding groove 18 along the circumference of the column section 17. The annular binding groove 18 has a diameter corresponding to the outer diameter of the coupling tube 25. When the coupling tube 25 is accommodated in the annular binding groove 18, the coupling tube 25 is restricted by the wall of the binding groove 18 to bind and tightly clamp the column section 17. Under such circumstance, the piston stem 15 can drive the needle holder 2 to move.

The inner circumference of rear section of the barrel 1 is formed with an annular rib 19. The piston stem 15 is formed with a protuberance 151. When the piston stem 15 is moved to a position where the column section 17 is inserted into the coupling tube 25 of the needle holder 2, while the coupling tube 25 is not accommodated in the annular binding groove 18, the protuberance 151 abuts against the annular rib 19 to locate the piston stem 15.

Figure 5:
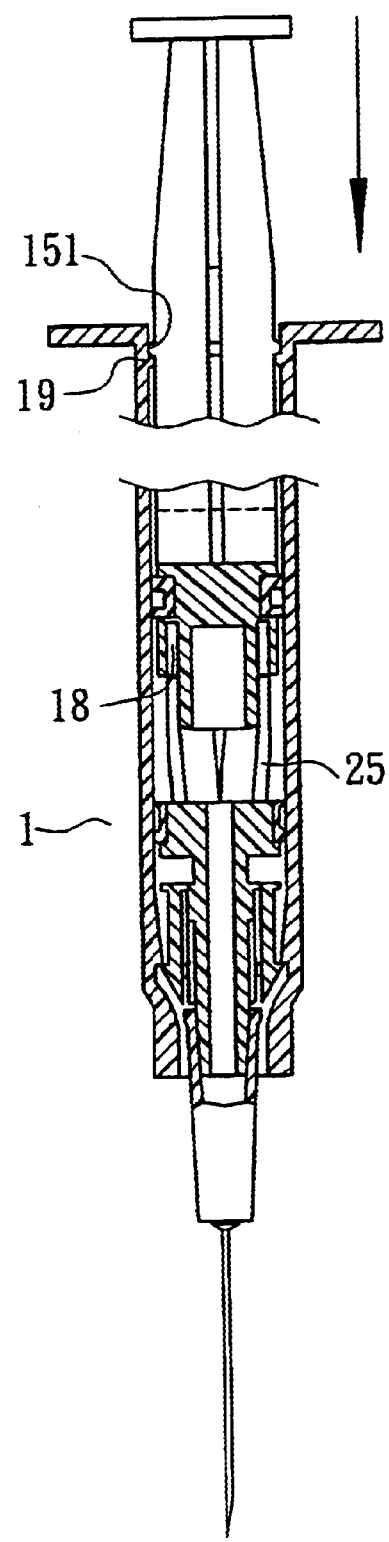
FIG. 5 is a sectional assembled view showing the use of the present invention.

The two click hooks 22 of the fixing ring 21 are engaged with the flange 11 of the barrel 1 to fix the needle holder 22 in the barrel 1. Therefore, prior to use, when the injection needle 24 is fitted onto the insertion tube 23, the needle holder 2 will not be pushed and moved. When the piston stem 15 is pushed forward prior to filling of the medicine or bleeding, the protuberance 151 will abut against the annular rib 19 of the barrel 1 to stop the coupling tube 25 from getting into the annular binding groove 18 to tightly clamp the column section 17 as shown in FIG. 5.

Figure 4:
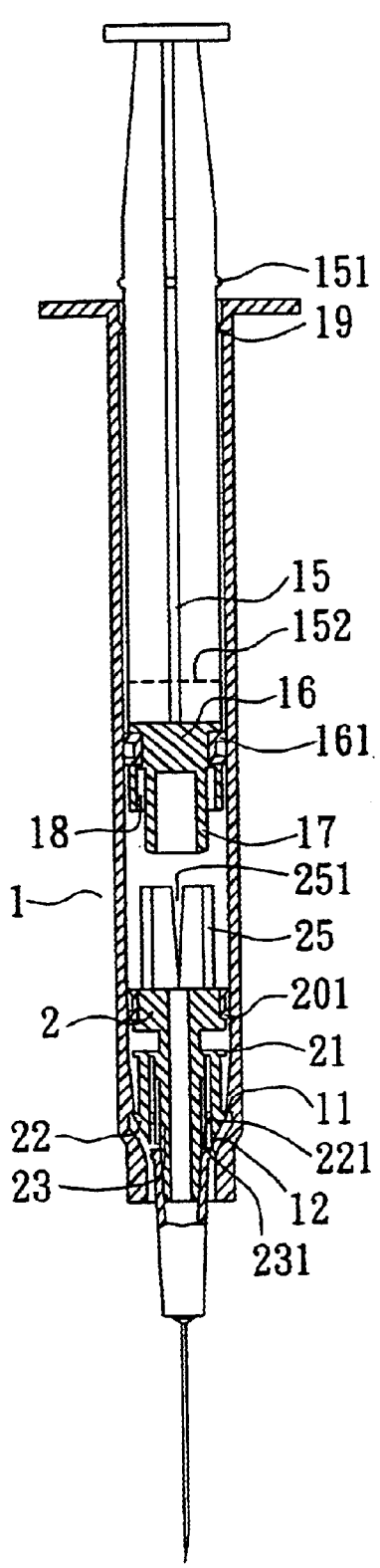
FIG. 4 is a sectional assembled view of the present invention.
Figure 6:
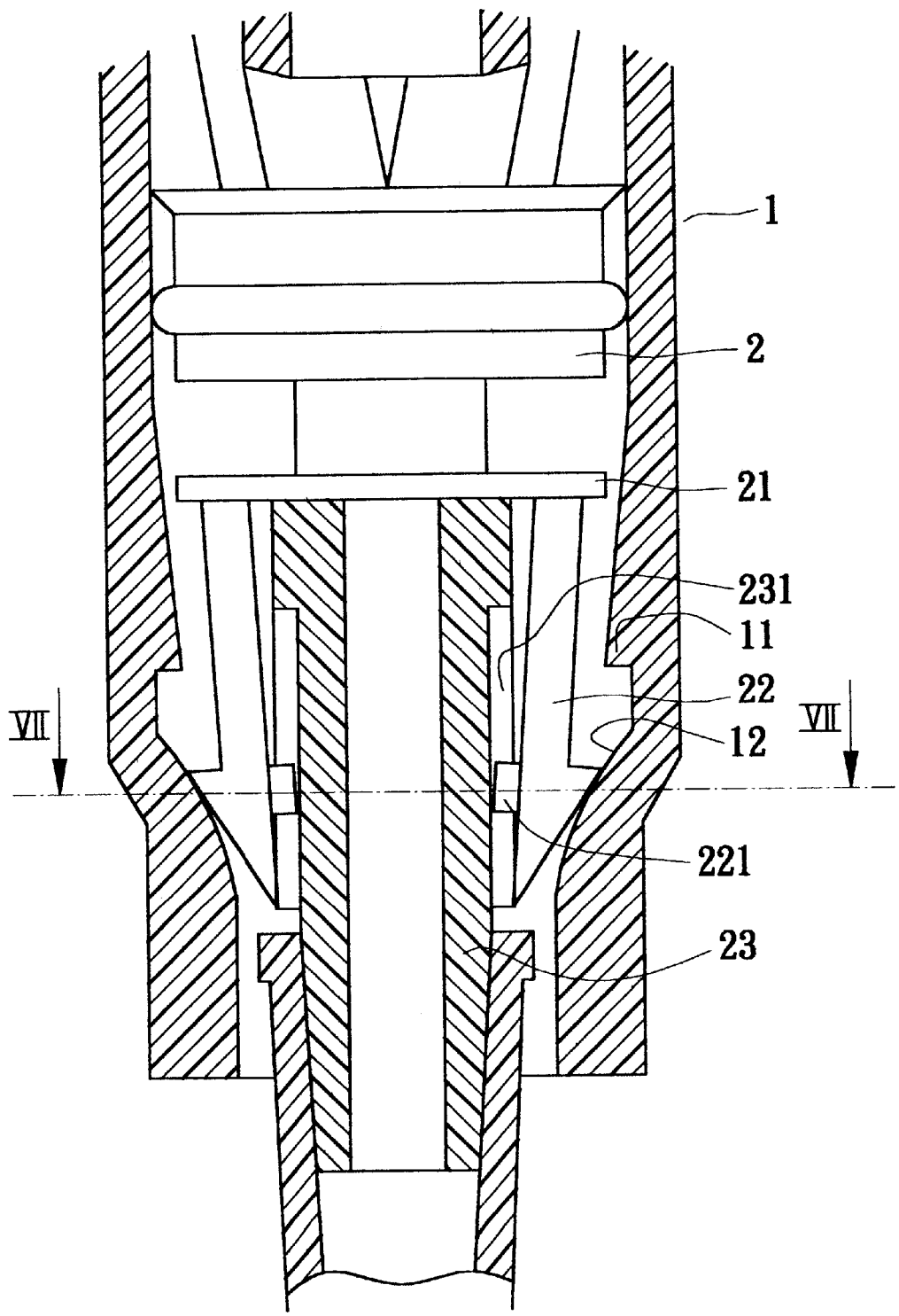
FIG. 6 is an enlarged view according to FIG. 5, showing the use of the present invention.
Figure 7:
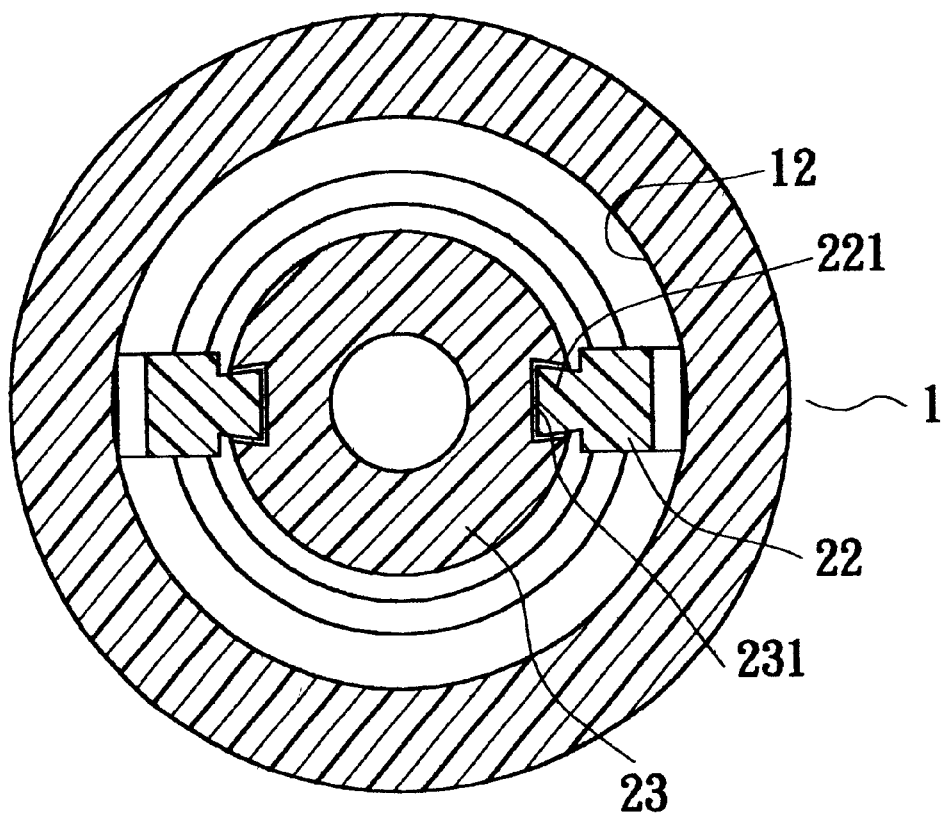
FIG. 7 is a sectional view taken along line VII—VII of FIG. 6.
Figure 8:
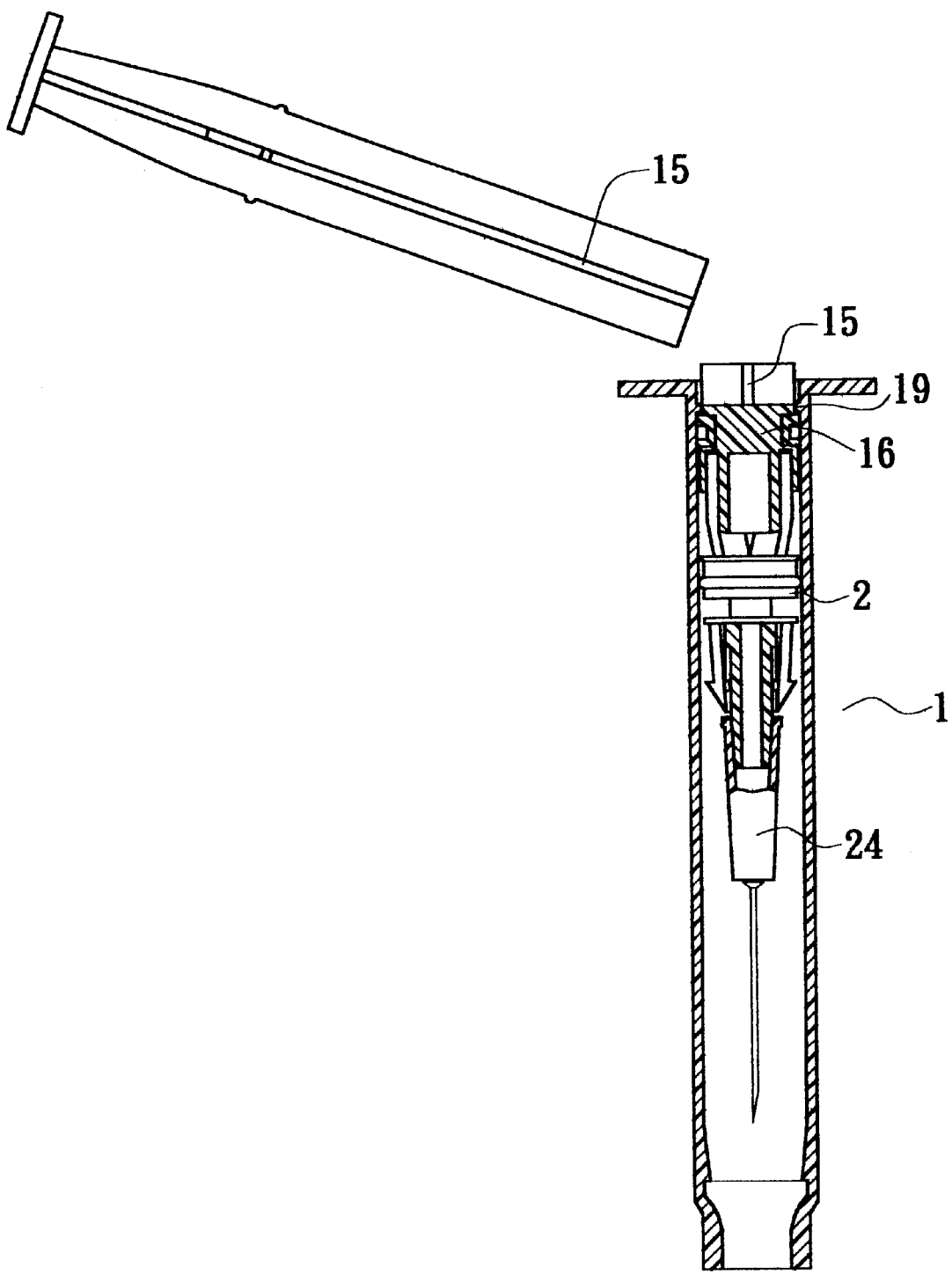
FIG. 8 is a sectional view showing that the piston stem is broken after the needle holder is retracted into the barrel of the present invention.

After use of the syringe, a user forward pushes the piston stem 15 and makes the protuberance 151 abut against the annular rib 19 of the barrel 1. At this time, the column section 17 is partially inserted into the coupling tube 25 which has multiple splits 251. Accordingly, after the column section 17 is inserted, the coupling tube 25 will be slightly expanded as shown in FIG. 4. When the user further forcedly pushes the piston stem 15 inward to make the protuberance 151 pass over the annular rib 19, the coupling tube 25 is accommodated into the annular binding groove 18 as shown in FIG. 6. At this time, the coupling tube 25 is restricted by the wall of the binding groove 18 to bind and tightly clamp the column section 17. Under such circumstance, the piston stem 15 is coupled with the needle holder 2. When the piston stem 15 is forcedly pushed inward to drive the needle holder 2, the click hooks 22 are pressed against the conic section 12 of front end of the barrel 1. At this time, the click hooks 22 are converged and the engaging blocks 221 are inlaid into the engaging channels 231 to locate the click hooks 22 as shown in FIG. 7. Accordingly, when the piston stem 15 is pulled rearward to drive the needle holder 2 to move rearward, the click hooks 22 can pass through the flange 11 and the needle holder 2 and the injection needle 24 can be retracted into the barrel 1. When the piston stem 15 is pulled rearward, the annular rib 19 will stop the piston 16 to prevent the piston 16 and the needle holder 2 from being extracted out of the barrel 1. The piston stem 15 is formed with a cut 152. When the piston 16 is engaged with the annular rib 19, the cut 152 is aligned with the bottom edge of the barrel 1, serving as a structurally weakened section. A user can break the piston stem 15 at the cut 152 as shown in FIG. 8. Accordingly, the piston 16, needle holder 2 and injection needle 24 are truly received in the barrel 1 to ensure safety.

The above embodiments are only used to illustrate the present invention, not intended to limit the scope thereof. Many modifications of the above embodiments can be made without departing from the spirit of the present invention.

What is claimed is:

1. A disposable safety syringe comprising:

a substantially tubular barrel, an inner circumference of a front section of the barrel being formed with an annular flange, the inner circumference of the barrel in front of the flange being further tapered to form a conic section;

a needle holder plugged in the front section of the barrel, the needle holder having a fixing ring having more than one click hook for hooking the flange of the barrel to locate the needle holder, the needle holder further having an insertion tube protruding from the needle holder for fitting with an injection needle, the insertion tube being formed with more than one engaging channel corresponding to the click hooks, the click hooks having a respective block corresponding to the engaging channels whereby the engaging blocks are inlaid in the engaging channels when the click hooks are located in the tapered section of the barrel and wherein the insertion tube inwardly extends to form a coupling tube having multiple axially extending splits; and a piston stem having a piston plugged in the barrel, a column section projecting from a front end of the piston, the column section having a diameter corresponding to an inner diameter of the coupling tube, whereby when inserted into the coupling tube, the column section can slightly expand the coupling tube, the front end of the piston being formed with an annular binding groove along the circumference of the column section, the annular binding groove having a diameter corresponding to an outer diameter of the coupling tube, when the coupling tube is accommodated in the annular binding groove, the coupling tube being restricted by the wall of the binding groove to bind and tightly clamp the column section, whereby the piston stem can drive the needle holder to move.

2. The disposable safety syringe as claimed in claim 1, wherein the inner circumference of a rear section of the barrel is formed with an annular rib and the piston stem is formed with a protuberance, whereby the protuberance abuts against the annular rib to locate the piston stem when the piston stem is moved to a position where the column section is inserted into the coupling tube of the needle holder such that the coupling tube is not accommodated in the annular binding groove and whereby after the piston stem is moved, such that the protuberance passes over the annular rib, the coupling tube is accommodated in the annular binding groove.

3. The disposable safety syringe as claimed in claim 1, wherein a sealing washer is provided between the needle holder and the inner circumference of the barrel.

4. The disposable safety syringe as claimed in claim 1, wherein a sealing washer is provided between the piston and the inner circumference of the barrel.

* * * * *